United States Patent [19]

Wikel

[11] Patent Number: 4,659,717
[45] Date of Patent: Apr. 21, 1987

[54] DIHYDROPYRIDINES USEFUL IN THE TREATMENT OF ANGINA AND STROKE

[75] Inventor: James H. Wikel, Greenwood, Ind.

[73] Assignee: Eli Lilly and Company, Indianapolis, Ind.

[21] Appl. No.: 768,071

[22] Filed: Aug. 21, 1985

[51] Int. Cl.⁴ .................... A61K 31/44; C07D 495/04
[52] U.S. Cl. .................... 514/301; 514/212; 514/300; 514/302; 514/316; 514/318; 514/337; 514/339; 540/597; 546/113; 546/114; 546/115; 546/116; 546/269; 546/273; 546/274
[58] Field of Search ............. 546/113, 114, 115, 116, 546/269, 273, 274; 260/244.4; 514/212, 300, 301, 302, 337, 339, 318, 316; 540/597

[56] References Cited

U.S. PATENT DOCUMENTS

| 4,258,042 | 3/1981 | Loev et al. | 424/248.5 |
| 4,380,547 | 4/1983 | Materne | 546/269 |
| 4,393,070 | 7/1983 | Sato et al. | 424/266 |
| 4,442,112 | 4/1984 | Muller-Schweinitzer | 424/263 |
| 4,472,584 | 9/1984 | Loev et al. | 546/321 |
| 4,492,703 | 1/1985 | Goldmann et al. | 424/266 |
| 4,497,821 | 2/1985 | Wehinger et al. | 514/302 |
| 4,500,528 | 2/1985 | Loev et al. | 514/228 |
| 4,500,532 | 2/1985 | Loev et al. | 514/256 |
| 4,503,223 | 3/1985 | Reilly | 544/122 |

FOREIGN PATENT DOCUMENTS 0088276 9/1983 European Pat. Off. .
2142021 1/1985 United Kingdom .

OTHER PUBLICATIONS

Treibs et al., Annalen, 652, pp. 192-203 (1962).
Derwent 83-766141/38, abstracting EPO 88,276.
Derwent 83-822231/47, abstracting EPO 94,159.

*Primary Examiner*—John M. Ford
*Assistant Examiner*—Bernard I. Dentz
*Attorney, Agent, or Firm*—Robert A. Conrad; Leroy Whitaker

[57] ABSTRACT

This invention provides certain substituted dihydropyridines, their pharmaceutical formulations, and their use for causing vasodilation in mammals.

20 Claims, No Drawings

DIHYDROPYRIDINES USEFUL IN THE TREATMENT OF ANGINA AND STROKE

BACKGROUND OF THE INVENTION

Organic nitrates, such as glyceryl trinitrate (nitroglycerin), have been used for many years as vasodilators, especially in the treatment of disease states such as angina pectoris. Although drugs such as nitroglycerin appear to be useful in treating the pain associated with angina, they sometimes increase the heart rate and generally have a short biological half-life and duration of action.

This invention provides certain dihydropyridine derivatives which are peripheral and cerebral vasodilators possessing bradycardic activity. This combination of activities provides compounds useful in treating disease states such as angina and stroke while counteracting and minimizing any reflex tachycardia.

SUMMARY OF THE INVENTION

This invention provides compounds of the formula wherein:

$R_1$ is hydrogen, $C_1$-$C_4$ alkyl, or each $R_2$ is independently hydrogen, methyl, or amino;

each $R_3$ is independently hydrogen, —$COR_7$, —$CO_2R_7$, or —$S(O)_nR_7$;

$R_4$ is hydrogen, methyl, methoxy, halo, nitro, or amino;

$R_5$ is hydrogen, methyl, methoxy, halo, or $C_1$-$C_4$ alkylthio;

$R_6$ is hydrogen, halo, $C_1$-$C_4$ alkoxy, $C_1$-$C_4$ alkyl, or nitro;

m is 0, 1, 2, 3, or 4;

Z is O, S, or NH;

three or four $A_1$, $A_2$, $A_3$, and $A_4$ are CH, and the remaining of $A_1$, $A_2$, $A_3$, and $A_4$, if any, is N;

$R_7$ is —alk—(Y—alk—)$_t$—$R_8$, allyl, propargyl, $C_3$-$C_6$ cycloalkyl, phenyl, or phenyl substituted with one to three substituents selected from $C_1$-$C_4$ alkyl, $C_1$-$C_4$ alkoxy, nitro, or halo;

each "alk" is a divalent organic radical derived from a $C_1$-$C_6$ aliphatic hydrocarbon;

Y is —O—, —NH—, or a bond;

t is 0 or 1;

$R_8$ is hydrogen, phenyl, pyridyl, —CN, or —$NR_9R_{10}$;

n is 0, 1, or 2; and $R_9$ and $R_{10}$ are independently $C_1$-$C_3$ alkyl or benzyl, or when taken together with the nitrogen atom to which they are attached form a pyrrolidone, piperidino, or homopiperidino ring, and pharmaceutically acceptable acid addition salts thereof.

This invention also provides a method of causing vasodilation in a mammal in need of such treatment which comprises administering to said mammal a vasodilating amount of a compound of the above formula. By virtue of their ability to cause vasodilation, the compounds of the above formula are useful in the treatment and prophylaxis of angina pectoris and stroke in mammals.

Further provided by this invention are pharmaceutical formulations comprising one or more of the compounds of the above formula in combination with a suitable pharmaceutical carrier, diluent, or excipient therefor. The formulations provided by this invention are particularly useful in treating mammals in need of vasodilation such as those suffering from or susceptible to angina pectoris or stroke.

DETAILED DESCRIPTION AND PREFERRED EMBODIMENTS

The following definitions refer to various terms used throughout this disclosure.

The term "$C_1$-$C_4$ alkyl" refers to the straight and branched aliphatic radicals of one to four carbon atoms such as methyl, ethyl, propyl, isopropyl, butyl, isobutyl, sec-butyl and tert-butyl. The term "$C_1$-$C_4$ alkyl" includes within its definition the term "$C_1$-$C_3$ alkyl".

The term "alk" refers to a divalent organic radical derived from a $C_1$-$C_6$ straight or branched aliphatic hydrocarbon such as —$CH_2$—, —$CH(CH_3)$—, —$C(CH_3)_2$—, —$CH(C_2H_5)$—, —$CH_2CH_2$—, —$CH_2CH(CH_3)$—, —$CH(CH_3)CH_2$—, —$CH(CH_3)CH(CH_3)$—, —$CH_2C(CH_3)_2$—, —$CH_2CH(C_2H_5)$—, —$CH_2CH_2CH_2$—, —$CH(CH_3)CH_2CH_2$—, —$CH_2CH(CH_3)CH_2$—, —$CH_2CH(C_2H_5)CH_2$— —$CH_2CH_2CH(C_2H_5)$—, —$CH(CH_3)CH_2CH(CH_3)$—, —$CH_2CH_2CH_2CH_2$—, —$CH_2C(CH_3)_2CH_2CH_2$—, —$CH_2CH_2CH(C_2H_5)CH_2$—, —$CH_2CH_2CH_2CH_2CH_2$, —$CH(CH_3)CH_2CH_2CH_2CH_2$—, —$CH_2CH_2CH_2CH_2CH_2CH_2$—, and the like.

The term "$C_3$-$C_6$ cycloalkyl" refers to saturated alicyclic rings of three to six carbon atoms such as cyclopropyl, methylcyclopropyl, cyclobutyl, cyclopentyl, cyclohexyl, and the like.

The term "$C_1$-$C_4$ alkoxy" refers to methoxy, ethoxy, propoxy, isopropoxy, butoxy, isobutoxy, sec-butoxy, and tert-butoxy. The term "$C_1$-$C_4$ alkylthio" refers to methylthio, ethylthio, propylthio, isopropylthio, butylthio, sec-butylthio, isobutylthio, and tert-butylthio.

The term "halo" refers to fluoro, chloro, bromo, and iodo. The term "pyridyl" refers to 2-, 3-, and 4-pyridyl.

According to the structure of formula I above, the group $R_4$ may be attached to any available carbon atom in the 6-membered ring of the bicyclic system. Similarly, the $R_5$ substituent may be attached to either available carbon atom of the 5-membered ring of the bicyclic nucleus. The dihydropyridine group may be attached to any available carbon atom of either ring of the bicyclic ring system.

As will be recognized by those skilled in the art, the compounds of formula I may contain one or more asymmetric carbon atoms. This invention is not limited to any particular isomer but includes all individual isomers as well as the racemates.

A preferred group of compounds of this invention are those wherein:
(a) $R_1$ is hydrogen,
(b) each $R_2$ group is methyl,
(c) each $R_3$ group is —$CO_2R_7$,
(d) $R_4$ is hydrogen,
(e) $R_5$ is hydrogen, and
(f) Z is S.

It is preferred that the dihydropyridine group be attached to one of the carbon atoms of the 5-membered ring of the bicyclic ring system. When one of $A_1$, $A_2$, $A_3$, and $A_4$ is N, the preferred positions are $A_2$ and $A_3$. A particularly preferred bicyclic ring system is a thieno[3,2-c]pyridin-3-yl group ($A_1=A_3=A_4=CH$; $A_2=N$; $Z=S$; $R_4=R_5=H$; and the dihydropyridine ring is attached at the 3-position).

The pharmaceutically acceptable acid addition salts of the bases represented by formula I can be prepared employing those acids of sufficient acidity to form acid addition salts. These acids include both inorganic and organic acids such as hydrochloric, hydrobromic, hydriodic, sulfuric, phosphoric, oxalic, methanesulfonic, benzenesulfonic, p-toluenesulfonic, maleic, and the like acids. Preferred acids for salt formation are the inorganic acids, especially hydrochloric acid.

The compounds of this invention may be prepared by any of a number of methods known in the art. For example, some of the compounds of formula I may be prepared by the reaction of intermediate II

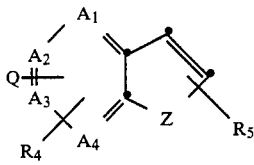

where Q is —CHO or —CHBr$_2$, with intermediate III $R_2COCH_2R_{3a}$      III where $R_{3a}$ is —$COR_7$, —$CO_2R_7$, or —$S(O)_nR_7$, and an amine intermediate of the formula $R_1$—$NH_2$. This reaction provides the compounds of formula I wherein neither $R_3$ is hydrogen. When the desired dihydropyridine is symmetrical, i.e., when both $R_2$ groups are the same and when both $R_{3a}$ groups are the same, the reaction is carried out employing two molar equivalents of III per equivalent of II. Alternatively, when the desired dihydropyridine is unsymmetrical, one equivalent each of two different intermediates III are reacted with an equivalent of II. In either reaction, at least one equivalent of $R_1$—$NH_2$ is employed. When $R_1$ is hydrogen, the ammonia source is usually an ammonium hydroxide solution.

The reaction is generally carried out in a non-reactive solvent such as an alcohol. When the amine used is aqueous ammonium hydroxide, the solvent should, of course, be miscible with the aqueous solution. The reaction is generally carried out at temperatures from about 20° C. up to the reflux temperature of the reaction mixture, for example about 80° C. When the preferred conditions of heating the reaction mixture to reflux in ethanol are employed, the reaction is generally complete within about 2-6 hours. When $R_2$ is hydrogen, intermediate III may be used either as the aldehyde or as an acetal derivative thereof.

Alternatively, the reaction with intermediates II may be carried out by using one equivalent of intermediate III and one equivalent of intermediate IV.

$R_2C(NHR_1)=CHR_{3a}$      IV

When this reaction sequence is performed, equimolar amounts of the three reactants are allowed to react under the same conditions as previously described in the absence of any other amine. Alternatively, the reaction can be performed using two equivalents of the same reagent IV or one equivalent each of two different intermediates IV while omitting intermediate III.

The compounds of formula I wherein either one or both of the $R_3$ substituents is hydrogen may be prepared from the carboxylic acid ester derivatives prepared by the above schemes (I, $R_3=$—$CO_2R_7$) by hydrolysis of one or both of the carboxylic esters according to standard procedures, followed by decarboxylation, also by known procedures. Alternatively, esters other than those defined by —$CO_2R_7$ may be employed, such as 2-cyanoethanol esters, which are more easily removed by basic or acidic hydrolysis. Other easily removable ester groups would be apparent to those skilled in the art.

In addition, when $R_1$ is hydrogen, compounds of formula I may be transformed into other compounds of formula I wherein $R_1$ represents substituents other than hydrogen. This reaction is a standard alkylation or arylation reaction and comprises treating compound I ($R_1$ is hydrogen) with a base of sufficient strength to remove the hydrogen atom and reacting the subsequent anion with the appropriate alkyl, aryl, or arylalkyl halide by methods well known in the art.

Intermediates II, III, and IV are commercially available, are known in the literature, or can be prepared by methods taught in the literature. For example, the aldehyde intermediates II (Q=—CHO) are available through a variety of chemical transformations. When the formyl group is on the carbon atom adjacent to the Z atom, the formyl group can be introduced directly upon treatment with dimethylformamide and a strong base such as lithium diisopropyl amide or n-butyl lithium. This reaction generally is performed at temperatures from about —40° to 0° C. in a non-reactive solvent such as diethyl ether or tetrahydrofuran. When the formyl group is on the other carbon atom of the 5-membered ring, the preferred route of introduction is according to the following scheme:

Scheme I

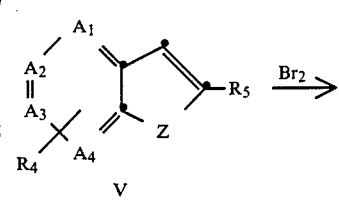

-continued
Scheme I

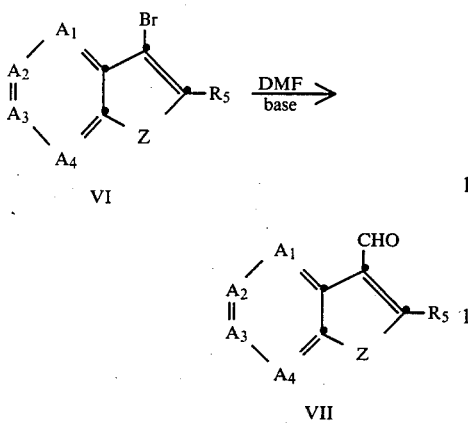

The bromo intermediate VI is prepared from the unsubstituted intermediate V by reaction with bromine in a non-reactive solvent such as carbon tetrachloride at a temperature from about 0°–40° C. This bromo intermediate is then transformed into aldehyde VII by treatment with dimethylformamide and a strong base such as n-butyl lithium and a non-reactive solvent such as diethyl ether or tetrahydrofuran, in a manner similar to that of introducing the formyl group to the position adjacent to the Z atom as previously described.

The preparation of the dibromomethyl intermediates (II, Q=—CHBr$_2$) is used especially for intermediates II wherein the Q substituent is attached to a carbon atom of the 6-membered ring. This dibromomethyl intermediate can be prepared from the corresponding methyl derivative upon treatment with excess N-bromosuccinimide in a non-reactive solvent such as carbon tetrachloride.

Other transformations of intermediates and final products are apparent to those skilled in the art. For example, nitro derivatives (I, R$_4$=nitro) are generally prepared from the corresponding intermediates II, wherein R$_4$ is hydrogen, by nitration of the ring. Standard nitration procedures usually produce a mixture of various nitro isomers, which may be resolved by standard methods such as liquid chromatography or crystallization. These nitro intermediates can then be transformed into the corresponding compounds of formula I wherein R$_4$ is nitro. The amino compounds of formula I are best prepared from the corresponding nitro compounds by standard hydrogenation procedures, such as hydrogenation in the presence of Raney nickel catalyst.

The introduction of various R$_5$ substituents can also be accomplished by methods known in the art. For example, intermediate V can be transformed into intermediate VI, wherein R$_5$ is bromo, by treatment with two equivalents of bromine in a non-reactive solvent such as chloroform. Other R$_5$ substituents can then be introduced. For example, treatment of intermediate VI (R$_5$ is bromo) with a strong base such as n-butyl lithium and a C$_1$-C$_4$ alkyl disulfide, in a non-reactive solvent such as diethyl ether or tetrahydrofuran, produces the corresponding intermediate VI wherein R$_5$ is C$_1$-C$_4$ alkylthio. This intermediate can be transformed into intermediate VII according to the reaction as described previously. Similarly, intermediate VI wherein R$_5$ is bromo may be treated first with a strong base such as n-butyl lithium followed by treatment with dimethylsulfate to provide the corresponding intermediate VI wherein R$_5$ is methyl. This intermediate likewise can be transformed to the aldehyde intermediate VII.

The following chemical examples are provided in order to further illustrate the preparation of the compounds of this invention. The examples are illustrative only and are not intended to limit the scope of the invention in any way.

EXAMPLE 1

4-Benzo[b]thien-2-yl-1,4-dihydro-2,6-dimethyl-3,5-pyridinedicarboxylic acid, diethyl ester A. Preparation of benzo[b]thiophene-2-carboxaldehyde.

To a solution of 31.25 ml of a 1.6M solution of n-butyl lithium in hexane and 100 ml of dry diethyl ether at −20° C. was added a solution of 6.7 g of 1-benzothiophene in 100 ml of dry diethyl ether. The mixture was stirred at −20° C. for 2 hours. A solution of 3.8 ml of dimethylformamide and 10 ml of dry diethyl ether was added and the reaction was allowed to warm to 0° C. The reaction was stirred an additional 1 hour at 0° C., at which time 75 ml of 1N hydrochloric acid were added. After stirring for 15 minutes, the layers were separated and the aqueous layer was extracted with diethyl ether. The combined organic extracts were dried over magnesium sulfate and evaporated to dryness. The resulting oil was stored at about 0° C. for 3 days, at which time a solid formed. The solid weighed 8.5 g and was identified as the desired subtitled intermediate based upon the mass spectral and proton NMR data.

Analysis for C$_9$H$_6$OS; Calculated: C, 66.64; H, 3,73; Found: C, 66.39; H, 3.95.

B. Preparation of 4-benzo[b]thien-2-yl-1,4-dihydro-2,6-dimethyl-3,5-pyridinedicarboxylic acid, diethyl ester.

A mixture of 3.24 g of benzo[b]thiophene-2-carboxaldehyde, 5.2 ml of ethyl acetoacetate, 2 ml of ammonium hydroxide, and 4 ml of ethanol was heated to reflux for 4 hours. The solution was concentrated in vacuo, at which time a yellow solid precipitated. The solid was recovered by filtration, providing 2.62 g of the desired title product, m.p. 167°–169° C.

Analysis for C$_{21}$H$_{23}$NO$_4$S; Calculated: C, 65.43; H, 6.01; N, 3.63; Found: C, 65.67; H, 6.00; N, 3.51.

EXAMPLE 2

1,4-Dihydro-2,6-dimethyl-4-(thieno[3,2-c]pyridin-2-yl)-3,5-pyridinedicarboxylic acid, diethyl ester The title product was prepared in 65% yield from the corresponding aldehyde intermediate following the procedures of Example 1, m.p.=203.5°–205° C.

Analysis for C$_{20}$H$_{22}$N$_2$O$_4$S; Calculated: C, 62.16; H, 5.74; N, 7.25; Found: C, 62.42; H, 5.52; N, 6.95.

EXAMPLE 3

4-Benzo[b]thien-3-yl-1,4-dihydro-2,6-dimethyl-3,5-pyridinedicarboxylic acid, diethyl ester A. Preparation of 3-bromobenzo[b]thiophene.

To a solution of 25 g of 1-benzothiophene in 100 ml of carbon tetrachloride at 15° C. were added 29.5 g of bromine over 6 hours. The reaction was allowed to stir at room temperature for 48 hours, at which time the reaction mixture was washed twice with a 1N aqueous sodium thiosulfate solution. The organic solution was dried over magnesium sulfate and evaporated to dryness. The resulting oil was vacuum distilled at 2 torr. Fractions collected between about 86°–90° L C. provided 27.7 g of the desired subtitle intermediate.

Analysis for $C_8H_5BrS$; Calculated: C, 45.09; H, 2.37; Found: C, 45.26; H, 2.36.

B. Preparation of benzo[b]thiophene-3-carboxaldehyde

To a solution of 17 ml of a 1.6M solution of n-butyl lithium in hexane and 100 ml of dry diethyl ether at −70° C. was added a solution of 5.3 g of 3-bromobenzo[b]thiophene in 65 ml of diethyl ether. After stirring for about 30 minutes, 2.2 ml of dry dimethylformamide in 2.5 ml of dry diethyl ether were added. The mixture was stirred for about 3.5 hours at −70° C., and then allowed to warm to −5° C. Approximately 100 ml of 1N hydrochloric acid were added and the reaction mixture was stirred at 0° C. for 15 minutes. The layers were separated and the aqueous layer was extracted with one liter of ether. The organic extracts were combined, dried over magnesium sulfate, and evaporated in vacuo. The resulting oil was held at 0° C. overnight at which time an orange solid had formed. Approximately 4.6 g of this solid was recovered and identified by proton NMR to be the desired subtitle carboxaldehyde intermediate. The carboxaldehyde intermediate was used without further purification.

C. Preparation of 4-benzo[b]thien-3-yl-1,4-dihydro-2,6-dimethyl-3,5-pyridinedicarboxylic acid, diethyl ester Following the procedure of Example 1B, 2.04 g of benzo[b]thiophene-3-carboxaldehyde, 3.2 ml of ethyl acetoacetate, and 1.5 ml of ammonium hydroxide were allowed to react in 15 ml of ethanol to provide 1.4 g of the desired title product, m.p. 139°–142° C.

Analysis for $C_{21}H_{23}NO_4S$; Calculated: C, 65.43; H, 6.01; N, 3.63; Found: C, 65.18; H, 5.96; N, 3.65.

EXAMPLES 4–14

Following the procedures of Example 3, the following compounds were prepared from the appropriate bromo intermediate and the corresponding β-keto ester. Yields are expressed as the percent molar yield from the aldehyde intermediate.

4. 4-(5-Chlorobenzo[b]thien-3-yl)-1,4-dihydro-2,6-dimethyl-3,5-pyridinedicarboxylic acid, diethyl ester, 86% yield, m.p. 154°–157° C.

Analysis for $C_{21}H_{22}ClNO_4S$; Calculated: C, 60.07; H, 5.24; N, 3.33; Found: C, 61.64; H, 5.38; N, 3.15.

5. 1,4-Dihydro-2,6-dimethyl-4-thieno[3,2-c]pyridin-3-yl-3,5-pyridinedicarboxylic acid, diethyl ester, 52% yield, m.p. 228°–231° C.

Analysis for $C_{20}H_{22}N_2O_4S$; Calculated: C, 62.16; H, 5.74; N, 7.25; Found: C, 62.05; H, 5.64; N, 7.24.

6. 1,4-Dihydro-2,6-dimethyl-4-(2-methylthieno[3,2-c]pyridin-3-yl)-3,5-pyridinedicarboxylic acid, diethyl ester, 18% yield, m.p.=252°–253° C.

Analysis for $C_{21}H_{24}N_2O_4S$; Calculated: C, 62.98; H, 6.04; N, 6.99; Found: C, 63.16; H, 6.25; N, 6.88.

7. 1,4-Dihydro-2,6-dimethyl-4-thieno[3,2-c]pyridin-3-yl-3,5-pyridinedicarboxylic acid, diisopropyl ester, 28% yield, m.p. 205°–206° C.

Analysis for $C_{22}H_{26}N_2O_4S$; Calculated: C, 63.75; H, 6.32; N, 6.76; Found: C, 64.03; H, 6.24; N, 6.78.

8. 1,4-Dihydro-2,6-dimethyl-4-thieno[3,2-c]pyridin-3-yl-3,5-pyridinedicarboxylic acid, bis(2-methoxyethyl)ester, 35% yield, m.p. 155°–157° C.

Analysis for $C_{22}H_{26}N_2O_6$; Calculated: C, 59.19; H, 5.83; N, 6.28; Found: C, 58.81; H, 5.93; N, 6.11.

9. 1,4-Dihydro-2,6-dimethyl-4-thieno[3,2-c]pyridin-3-yl-3,5-pyridinedicarboxylic acid, dimethyl ester, 59% yield, m.p. 238°–241° C.

Analysis for $C_{18}H_{18}N_2O_4S$; Calculated: C, 60.32; H, 5.06; N, 7.82; Found: C, 60.55; H, 5.13; N, 7.94.

10. 1,4-Dihydro-2,6-dimethyl-4-thieno[3,2-c]pyridin-3-yl-3,5-pyridinedicarboxylic acid, dipropyl ester, 53% yield, m.p. 174°–176° C.

Analysis for $C_{22}H_{26}N_2O_4S$; Calculated: C, 63.75; H, 6.32; N, 6.76; Found: C, 63.81; H, 6.48; N, 6.67.

11. 1,4-Dihydro-2,6-dimethyl-4-thieno[3,2-b]pyridin-3-yl-3,5-pyridinedicarboxylic acid, diethyl ester, 36% yield, m.p. 172.5°–174° C.

Analysis for $C_{20}H_{22}N_2O_4S$; Calculated: C, 62.16; H, 5.74; N, 7.25; Found: C, 62.31; H, 6.01; N, 7.29.

12. 1,4-Dihydro-2,6-dimethyl-4-thieno[2,3-c]pyridin-3-yl-3,5-pyridinedicarboxylic acid, diethyl ester, 37% yield, m.p. 198°–200° C.

Analysis for $C_{20}H_{22}N_2O_4S$; Calculated: C, 62.16; H, 5.74; N, 7.25; Found: C, 61.90; H, 6.00; N, 7.13.

13. 1,4-Dihydro-2,6-dimethyl-4-thieno[2,3-b]pyridin-3-yl-3,5-pyridinedicarboxylic acid, diethyl ester, 40% yield, m.p. 190°–193° C.

Analysis for $C_{20}H_{22}N_2O_4S$; Calculated: C, 62.16; H, 5.74; N, 7.25; Found: C, 61.98; H, 5.79; N, 7.11.

14. 1,4-Dihydro-2,6-dimethyl-4-(7-methylthieno[2,3-c]pyridin-3-yl)-3,5-pyridinedicarboxylic acid, diethyl ester, 8% yield, m.p. 199°–202° C.

Analysis for $C_{21}H_{24}N_2O_4S$; Calculated: C, 62.98; H, 6.04; N, 6.99; Found: C, 62.72; H, 5.92; N, 6.71.

EXAMPLE 15

1,4-Dihydro-2,6-dimethyl-4-[2-(methylthio)benzo[b]thien-3-yl]-3,5-pyridinedicarboxylic acid, diethyl ester A. Preparation of 2,3-dibromobenzo[b]thiophene.

A solution of 64 g of bromine in 50 ml of chloroform was added to a solution of 26.8 g of 1-benzothiophene in 150 ml of chloroform. After stirring for approximately 18 hours, the reaction mixture was washed sequentially with 0.1N sodium hydroxide, 0.1N aqueous sodium thiosulfate, and water. The organic layer was dried over magnesium sulfate and evaporated to dryness. The residue was crystallized twice from methanol to provide 20.54 g of the desired subtitled intermediate, m.p. 57°–59° C.

Analysis for $C_8H_4Br_2S$; Calculated: C, 32.91; H, 1.38; Found: C, 32.72; H, 1.49.

B. Preparation of 3-bromo-2-(methylthio)benzo[b]thiophene.

A solution of 8.76 g of 2,3-dibromobenzo[b]thiophene in 75 ml of diethyl ether was cooled to 0° C. and 19 ml of a 1.6M solution of n-butyl lithium in hexane and 10 ml of diethyl ether were added. A pink slurry formed which was stirred for one hour. A solution of 2.7 ml of methyl disulfide in 10 ml of diethyl ether was added and the reaction mixture was stirred for 4 hours at 0° C. Approximately 100 ml of 1N hydrochloric acid were added and the reaction was allowed to warm to room temperature. The layers were separated and the aqueous layer was extracted with diethyl ether. The combined organic extracts were dried over magnesium sulfate and evaporated to dryness. The resulting oil was vacuum distilled at 1.5 torr providing 1 g of the desired subtitled intermediate.

Analysis for C$_9$H$_7$BrS$_2$; Calculated: C, 41.71; H, 2.72; S, 25.00; Found: C, 42.00; H, 3.02; S, 24.74.

C. Preparation of 2-(methylthio)benzo[b]thiophene-3-carboxaldehyde.

Following the general procedure of Example 3B, 3 g of 3-bromo-2-(methylthio)benzo[b]thiophene were converted into 1.4 g of the desired subtitle intermediate, m.p. 50°–53° C. The proton NMR spectrum was consistent with the structure of the desired intermediate.

Analysis for C$_{10}$H$_8$OS$_2$Calculated: C, 57.66; H, 3.87; Found: C, 55.99; H, 3.89.

D. Preparation of 1,4-dihydro-2,6-dimethyl-4-[2-(methylthio)benzo[b]thien-3-yl]-3,5-pyridinedicarboxylic acid, diethyl ester.

Following the general procedure of Example 1B, 0.9 g of 2-(methylthio)benzo[b]thiophene-3-carboxaldehyde, 1.1 ml of ethyl acetoacetage, and 0.5 ml of ammonium hydroxide were reacted to provide 0.48 g of the desired title product, m.p. 177°–179° C.

Analysis for C$_{22}$H$_{25}$NO$_4$S$_2$; Calculated: C, 61.23; H, 5.84; N, 3.25; Found: C, 61.45; H, 5.68; N, 3.32.

EXAMPLE 16

1,4-Dihydro-2,6-dimethyl-4-(2-methylbenzo[b]thien-3-yl)-3,5-pyridinedicarboxylic acid, diethyl ester

A. Preparation of 2-methyl-3-bromobenzo[b]thiophene.

To a solution of 15.88 g of 2,3-dibromobenzo[b]thiophene in 150 ml of dry diethyl ether at 0° C. was added a solution of 20 ml of diethyl ether and 34 ml of a 1.6M solution of n-butyl lithium in hexane. After stirring for one hour at 0° C., a solution of 10.2 ml of dimethylsulfate in 20 ml of diethyl ether was added and the reaction was stirred at 0° C. for 4 hours. The mixture was allowed to warm to room temperature. After the addition of 125 ml of 1N hydrochloric acid, the reaction mixture was stirred for 15 minutes. The layers were separated and the aqueous layer was extracted with diethyl ether. The combined ether extracts were dried over magnesium sulfate and evaporated in vacuo giving an oil. The oil was cooled and it solidified. The resulting crystals were recovered by filtration providing 8.7 g of the desired subtitled intermediate, m.p. 39°–40° C.

Analysis for C$_9$H$_7$BrS; Calculated: C, 47.59; H, 3.11; Found: C, 48.77; H, 2.80.

B. Preparation of 2-methylbenzo[b]thiophene-3-carboxaldehyde.

Following the general procedure of Example 3B, 2 g of 2-methyl-3-bromobenzo[b]thiophene were transformed into 0.6 g of the desired subtitled intermediate, m.p. 95°–96° C.

Analysis for C$_{10}$H$_8$OS; Calculated: C, 68.15; H, 4.58; Found: C, 69.07; H, 4.84.

C. Preparation of 1,4-dihydro-2,6-dimethyl-4-(2-methylbenzo[b]thien-3-yl)-3,5-pyridinedicarboxylic acid, diethyl ester.

A mixture of 2.2 g of 2-methylbenzo[b]thiophene-3-carboxaldehyde, 4.9 g of ethyl 3-aminocrotonate, and 10 ml of ethanol were heated to reflux for approximately 18 hours. An additional 1.6 g of ethyl 3-aminocrotonate were added and the reaction was heated an additional 24 hours at reflux. The reaction mixture was cooled and concentrated and the resulting solid was recovered by filtration providing 2.15 g of the desired title product, m.p. 191°–193° C.

Analysis for C$_{22}$H$_{25}$NO$_4$S; Calculated: C, 66.14; H, 6.31; N, 3.51; Found: C, 65.87; H, 6.49; N, 3.63.

EXAMPLE 17

1,4-Dihydro-2,6-dimethyl-4-thieno[3,2-c]pyridin-3-yl-3,5-pyridinedicarboxylic acid, 3-ethyl 5-isopropyl ester A solution of 1 g of thieno[3,2-c]pyridine-3-carboxaldehyde, 1.08 g of isopropyl acetoacetate, and 0.9 g of ethyl 3-aminocrotonate in 4 ml of ethanol was heated to reflux for approximately 18 hours. Upon cooling, a solid formed which was recovered by filtration providing 0.73 g of the desired title product, m.p. 212°–215° C.

Analysis for C$_{21}$H$_{24}$N$_2$O$_4$S; Calculated: C, 62.98; H, 6.04; N, 6.99; Found: C, 62.79; H, 5.75; N, 7.17.

EXAMPLES 18–20

The following compounds were prepared according to the procedure of Example 17 using the appropriate aldehyde, alkyl 3-aminocrotonate, and acetoacetate derivatives.

18. 4-Benzo[b]thien-3-yl-1,4-dihydro-2,6-dimethyl-3,5-pyridinedicarboxylic acid, 3-ethyl 5-(2-[methyl(phenylmethyl)amino]ethyl)ester, 0.2% yield, oil.

Analysis for C$_{29}$H$_{32}$N$_2$O$_4$S; Calculated: C, 69.02; H, 6.39; N, 5.55; Found: C, 68.81; H, 6.41; N, 5.32.

19. 1,4-Dihydro-2,6-dimethyl-4-thieno[3,2-]pyridin-3-yl-3,5-pyridinedicarboxylic acid, 3-ethyl 5-(2-methoxyethyl)ester, 3% yield, m.p. 180°–182° C.

Analysis for C$_{21}$H$_{25}$N$_2$O$_5$S; Calculated: C, 60.41; H, 6.04; N, 6.71; Found: C, 60.56; H, 5.84; N, 6.60.

20. 1,4-Dihydro-2,6-dimethyl-4-thieno[3,2-c]pyridin-3-yl-3,5-pyridinedicarboxylic acid, 3-methyl 5-isopropyl ester, 6% yield, m.p. 215°–218° C.

Analysis for C$_{20}$H$_{22}$N$_2$O$_4$S; Calculated: C, 62.17; H, 5.69; N, 7.25; Found: C, 61.78; H, 5.88; N, 7.01;

EXAMPLE 21

1,4-Dihydro-2,6-dimethyl-4-thieno[3,2-c]pyridine-3-yl-3,5-pyridinedicarboxylic acid, 3-methyl 5-(2-methoxyethyl)ester A solution of 1 g of thieno[3,2-c]pyridine-3-carboxaldehyde, 1.2 g of 2-methoxyethyl acetoacetate, 0.75 ml of methyl acetoacetate, and 2 ml of ammonium hydroxide were heated to reflux for approximately 18 hours. The solvent was removed in vacuo and the resulting oil was purified by chromatography over silica gel eluting with a methylene chloride/ethyl acetate step gradient. The appropriate fractions were combined, the solvents were evaporated, and the resulting oil was triturated with diethyl ether providing 0.2 g of the desired title product, m.p. 170°–173° C.

Analysis for C$_{20}$H$_{22}$N$_2$O$_5$S; Calculated: C, 59.69; H, 5.54; N, 6.96; Found: C, 59.51; H, 5.49; N, 7.21.

EXAMPLE 22

4-(5-Bromobenzo[b]thien-3-yl)-1,4-dihydro-2,6-dimethyl-3,5-pyridinedicarboxlic acid, diethyl ester

A. Preparation of 5-bromo-3-(dibromomethyl)benzo[b]thiophene.

A solution of 1.44 g of 5-bromo-3-methylbenzo[b]thiophene and 2.5 g of N-bromosuccinimide in 25 ml of carbon tetrachloride was heated to reflux for 12 hours. The reaction mixture was filtered and the filtrate was evaporated to provide the subtitle intermediate as an oil which was used without further purification.

B. Preparation of 4-(5-bromobenzo[b]thien-3-yl)-1,4-dihydro-2,6-dimethyl-3,5-pyridinedicarboxylic acid, diethyl ester.

A mixture of 2.35 g of 5-bromo-3-(dibromomethyl)-benzo[b]thiophene and 1.6 g of ethyl 3-aminocrotonate in 4 ml of ethanol was heated to reflux for 14 hours. The mixture was evaporated in vacuo and the residue was purified by chromatography over silica gel to provide 0.8 g of the desired title product, m.p. 68°–70° C.

Analsysis for $C_{21}H_{22}BrNO_4S$; Calculated: C, 54.32; H, 4.78; N, 3.02; Found: C, 54.57; H, 4.68; N, 2.90.

EXAMPLES 23–24

The following compounds were prepared from the corresponding dibromomethyl intermediate according to the procedure of Example 22 using either the same ethyl 3-aminocrotonate procedure or ethyl acetoacetate and ammonium hydroxide in either ethanol or toluene.

23. 4-(2-Bromobenzo[b]thien-3-yl)-1,4-dihydro-2,6-dimethyl-3,5-pyridinedicarboxylic acid, diethyl ester, 28% yield, m.p.=68°–70° C.

Analysis for $C_{21}H_{22}BrNO_4S$; Calculated: C, 54.31; H, 4.74; N, 3.02; Found: C, 54.51; H, 4.74; N, 2.90.

24. 1,4-Dihydro-2,6-dimethyl-4-thieno[2,3-c]pyridin-7-yl-3,5-pyridinedicarboxylic acid, diethyl ester, 15% yield, m.p. 205°–210° C. with decomposition. The NMR and mass spectral analyses of the product were consistent with the proposed structure of the desired product.

Analysis for $C_{20}H_{22}N_2O_4S$; Calculated: C, 62.16; H, 5.74; N, 7.25; Found: C, 58.85; H, 5.65; N, 7.21.

EXAMPLE 25

1,4-Dihydro-2,6-dimethyl-4-(7-nitrobenzo[b]thien-3-yl)-3,5-pyridinedicarboxylic acid, diethyl ester

A. Preparation of nitrobenzo[b]thiophene-3-carboxaldehydes.

Twenty-five grams of benzo[b]thiophene-3-carboxyaldehyde were added to 375 ml of 70% nitric acid at 0° C. After stirring for 48 hours at room temperature, a bright yellow slurry was obtained. The slurry was filtered and the recovered solid was crystallized from acetonitrile to provide 12.36 g of 6-nitrobenzo[b]thiophene-3-carboxaldehyde.

The filtrate from the above reaction was treated with 1 liter of water and the resulting slurry was filtered providing 19 g of a mixture of the 5- and 7-nitro isomers. Six grams of this mixture were purified by chromatography over silica gel providing 2.08 g of 7-nitrobenzo[b]thiophene-3-carboxaldehyde and 2.0 g of 5-nitrobenzo[b]thiophene-3-carboxaldehyde. CL B. Preparation of 1,4-dihydro-2,6-dimethyl-4-(7-nitrobenzo[b]thien-3-yl)-3,5-pyridinedicarboxylic acid, diethyl ester.

Following the procedure of Example 1B, 1.3 g of 7-nitrobenzo[b]thiophene-3-carboxaldehyde were converted into 0.7 g of the desired title product, m.p. 205°–206° C.

Analysis for $C_{21}H_{22}N_2O_6S$; Calculated: C, 58.59; H, 5.15; N, 6.51; Found: C, 58.57; H, 5.02; N, 6.38.

EXAMPLE 26

1,4-Dihydro-2,6-dimethyl-4-(5-nitrobenzo[b]thien-3-yl)-3,5-pyridinedicarboxylic acid, diethyl ester The title compound was prepared in 32% yield from 5-nitrobenzo[b]thiophene-3-carboxaldehyde following the procedure of Example 1B. The product had a melting point of 255°–259° C.

Analysis for $C_{21}H_{22}N_2O_6S$; Calculated: C, 58.59; H, 5.15; N, 6.51; Found: C, 58.64; H, 5.05; N, 6.38.

EXAMPLE 27

1,4-Dihydro-2,6-dimethyl-4-(6-nitrobenzo[b]thien-3-yl)-3,5-pyridinedicarboxylic acid, diethyl ester

A. Preparation of nitrobenzo[b]thiophene-3-carboxaldehydes.

A solution of 9 g of benzo[b]thiophene-3-carboxaldehyde in 50 ml of acetic anhydride was cooled to 0° C. by means of an external ethanol/ice bath. A solution of 40 ml of acetic acid and 20 ml of fuming nitric acid was added at such a rate to maintain the temperature of the reaction at 0°–5° C. Following the addition of the reagents, the reaction mixture was stirred for 1.5 hours. The reaction mixture was poured into 500 ml of ice and extracted with ethyl acetate. The organic layer was washed with water, dried over magnesium sulfate, and evaporated in vacuo. The resulting oil was treated with ethanol. A solid formed, which was recovered by filtration providing 1.3 g of 6-nitrobenzo[b]thiophene-3-carboxaldehyde, m.p. 187°–192° C.

The ethanol filtrate was evaporated providing an oil which was purified by chromatography over silica gel eluting with cyclohexane. Fractions containing impure 4-nitro compound were combined and evaporated to provide 1.5 g of material which was rechromatographed over silica gel eluting with 9:1 cyclohexane:-methylene chloride. The appropriate fractions were collected and evaporated to provide 0.3 g of the desired 4-nitrobenzo[b]thiophene-3-carboxaldehyde.

B. Preparation of 1,4-dihydro-2,6-dimethyl-4-(6-nitrobenzo[b]thien-3-yl]-3,5-pyridinedicarboxylic acid, diethyl ester.

Following the procedure of Example 16C, 0.5 g of 6-nitrobenzo[b]thiophene-3-carboxaldehyde and 0.7 g of ethyl 3-aminocrotonate were reacted to provide 0.4 g of the desired title product, m.p. 191°–194° C.

Analysis for $C_{21}H_{22}N_2O_6S$; Calculated: C, 58.59; H, 5.15; N, 6.51; Found: C, 58.65; H, 5.22; N, 6.78.

EXAMPLE 28

1,4-Dihydro-2,6-dimethyl-4-(4-nitrobenzo[b]thien-3-yl)-3,5-pyridinecarboxylic acid, diethyl ester Following the general procedure of Example 1B, 0.27 g of 4-nitrobenzo[b]thiophene-3-carboxaldehyde, 0.4 ml of ethyl acetoacetate, and 1 ml of ammonium hydroxide were reacted to provide 0.17 g of the desired title product, m.p. 178°–181° C.

Analysis for $C_{21}H_{22}N_2O_6S$; Calculated: C, 58.59; H, 5.15; N, 6.51; Found: C, 58.32; H, 5.34; N, 6.41.

EXAMPLE 29

4-(6-Aminobenzo[b]thien-3-yl)-1,4-dihydro-2,6-dimethyl-3,5-pyridinecarboxylic acid, diethyl ester One gram of 1,4-dihydro-2,6-dimethyl-4-(6-nitrobenzo[b]thien-3-yl)-3,5-pyridinecarboxylic acid, diethyl ester was hydrogenated overnight at room temperature in 98 ml of ethanol in the presence of 1 g of 5% palladium-on-carbon. The mixture was filtered and the filtrate was evaporated in vacuo providing 0.8 g of the desired title product, m.p. 171°–175° C.

Analysis for $C_{21}H_{24}N_2O_4S$; Calculated: C, 62.98; H, 6.04; N, 6.99; Found: C, 62.24; H, 6.42; N, 6.87.

EXAMPLE 30

4-(7-Aminobenzo[b]thien-3-yl)-1,4-dihydro-2,6-dimethyl-3,5-pyridinecarboxylic acid, diethyl ester Following the procedure of Example 29, 0.7 g of 1,4-dihydro-2,4-dimethyl-4-(7-nitrobenzo[b]thien-3-yl)-3,5-pyridinecarboxylic acid, diethyl ester were hydrogenated to produce 0.55 g of the desired title product, m.p. 75°–78° C.

Analysis for $C_{21}H_{24}N_2O_4S$; Calculated: C, 62.98; H, 6.04; N, 6.99; Found: C, 62.78; H, 6.26; N, 6.26.

EXAMPLE 31

1,4-Dihydro-2,6-dimethyl-4-thieno[3,2-c]pyridin-3-yl-3,5-pyridine dicarboxylic acid, 3-methyl 5-(2-[methyl(phenylmethyl)amino]ethyl)ester Following the procedure of Example 17, 1.6 g of thieno[3,2-c]pyridine-3-carboxaldehyde, 2.45 g of (N-benzyl-N-methyl-2-aminoethyl)acetoacetate, and 1.13 g of methyl 3-aminocrotonate were allowed to react at reflux. Chromatography of the product and crystallization from diethyl ether/hexane provided 0.67 g of the desired title product, m.p. 153°–154° C.

Analysis for $C_{27}H_{29}N_3O_4S$; Calculated: C, 65.97; H, 5.95; N, 8.55; Found: C, 65.82; H, 5.84; N, 8.54.

EXAMPLE 32

4-(Benzo[b]thien-3-yl)-1,4-dihydro-2,6-dimethyl-3,5-pyridinedicarboxylic acid, bis(2-[methyl(phenylmethyl)amino]ethyl ester The title compound was prepared in 36.9% yield as an oil from 1.62 g of benzo[b]thiophene-3-carboxaldehyde and 5.0 g of N-benzyl-N-methyl-2-aminoethyl acetoacetate following the procedure of Example 1B. The mass spectral analysis was consistant with the desired product.

Analysis for $C_{37}H_{41}N_3O_4S$; Calculated: C, 71.24; H, 6.63; N, 6.74; Found: C, 72.99; H, 7.03; N, 6.11.

EXAMPLES 33–51

The following compounds were prepared according to the procedure of Example 17 from the appropriate carboxaldehyde, aminocrotonate, and acetoacetate intermediates.

33. 1,4-Dihydro-2,6-dimethyl-4-thieno[3,2-c]pyridin-3-yl-3,5-pyridinedicarboxylic acid, ethyl methyl ester, 24% yield, m.p. 218°–220° C.

Analysis for $C_{19}H_{20}N_2O_4S$; Calculated: C, 61.27; H, 5.41; N, 7.52; Found: C, 61.16; H, 5.24; N, 7.58.

34. 1,4-Dihydro-2,6-dimethyl-4-thieno[3,2-c]pyridin-3-yl-3,5-pyridinedicarboxylic acid, 2-cyanoethyl methyl ester, 25% yield, m.p. 208°–209° C. with decomposition.

Analysis for $C_{20}H_{19}N_3O_4S$; Calculated: C, 60.44; H, 4.82; N, 10.57; Found: C, 60.27; H, 4.69; N, 10.38.

35. 4-Benzo[b]thien-3-yl-1,4-dihydro-2,6-dimethyl-3,5-pyridinecarboxylic acid, 2-cyanoethyl methyl ester, 41.6% yield, oil.

Analysis for $C_{21}H_{20}N_2O_4S$; Calculated: C, 63.62; H, 5.08; N, 7.07; Found: C, 61.31; H, 5.23; N, 7.82.

36. (S)-4-benzo[b]thien-3-yl-1,4-dihydro-2,6-dimethyl-3,5-pyridinedicarboxylic acid, methyl 1-methylpropyl ester, 47.6% yield, oil?, $\alpha_D = +13.93°$ (C = 10.05, Methanol)

Analysis for $C_{22}H_{25}NO_4S$; Calculated: C, 66.14; H, 6.31; N, 3.51; Found: C, 66.04; H, 6.48; N, 3.76.

37. 1,4-Dihydro-2,6-dimethyl-4-thieno[3,2-c]pyridin-3-yl-3,5-pyridinedicarboxylic acid, 2-methoxyethyl 1-methylethyl ester, 42% yield, m.p. 189°–194° C.

Analysis for $C_{22}H_{26}N_2O_5S$; Calculated: C, 61.38; H, 6.09; N, 6.51; Found: C, 61.22; H, 5.93; N, 6.65.

38. 4-Benzo[b]thien-3-yl-1,4-dihydro-2,6-dimethyl-3,5-pyridinedicarboxylic acid, methyl 1-methylethyl ester, 80% yield, m.p. 130°–142° C. The mass spectrum was consistent with the structure of the desired compound.

39. 4-Benzo[b]thien-3-yl-1,4-dihydro-2,6-dimethyl-3,5-pyridinedicarboxylic acid, 2-methoxyethyl 1-methylethyl ester, 51% yield, oil.

Analysis for $C_{23}H_{27}NO_5S$; Calculated: C, 64.31; H, 6.34; N, 3.26; Found: C, 64.61; H, 6.13; N, 3.39.

40. 1,4-Dihydro-2,6-dimethyl-4-thieno[3,2-c]pyridin-3-yl-3,5-pyridinedicarboxylic acid, methyl(S)-1-methylpropyl ester, 37.4% yield, m.p. 208°–210° C. with decomposition.

Analysis for $C_{21}H_{25}N_2O_4S$; Calculated: C, 62.82; H, 6.28; N, 6.98; Found: C, 62.58; H, 6.10; N, 6.87.

41. 1,4-Dihydro-2,6-dimethyl-4-thieno[2,3-c]pyridin-3-yl-3,5-pyridinedicarboxylic acid, monomethyl mono(1-methylethyl)ester, 1% yield, m.p. 166°–168° C.

Analysis for $C_{20}H_{22}N_2O_4S$; Calculated: C, 62.16; H, 5.74; N, 7.25; Found: C, 61.89; H, 5.87; N, 7.46.

42. (R)-1,4-Dihydro-2,6-dimethyl-4-thieno[3,2-c]pyridin-3-yl-3,5-pyridinedicarboxylic acid, methyl 1-methylpropyl ester, 50% yield, m.p. 196°–198° C.

Analysis for $C_{21}H_{25}N_2O_4S$; Calculated: C, 62.82; H, 6.28; N, 6.98; Found: C, 63.03; H, 5.90; N, 6.95.

43. 1,4-Dihydro-2,6-dimethyl-4-thieno[3,2-c]pyridin-3-yl-3,5-pyridinedicarboxylic acid, methyl 2-methylpropyl ester, 67% yield, m.p. 169°–171° C. with decomposition.

Analysis for $C_{21}H_{25}N_2O_4S$; Calculated: C, 62.82; H, 6.28; N, 6.98; Found: C, 62.58; H, 6.05; N, 7.08.

44. 1,4-Dihydro-2,6-dimethyl-4-thieno[2,3-c]pyridin-3-yl-3,5-pyridinedicarboxylic acid, cyclopropylmethyl methyl ester, 43% yield, m.p. 179°–181° C.

Analysis for $C_{21}H_{22}N_2O_4S$; Calculated: C, 63.30; H, 5.57; N, 7.03; Found: C, 63.53; H, 5.83; N, 7.31.

45. 1,4-Dihydro-2,6-dimethyl-4-thieno[3,2-c]pyridin-3-yl-3,5-pyridinedicarboxylic acid, methyl 1,1-dimethylethyl ester, 17% yield, m.p. 225°–227° C.

Analysis for $C_{21}H_{24}N_2O_4S$; Calculated: C, 62.98; H, 6.04; N, 6.99; Found: C, 62.73; H, 5.86; N, 7.06.

46. 1,4-Dihydro-2,6-dimethyl-4-thieno[3,2-b]pyridin-3-yl-3,5-pyridinedicarboxylic acid, cyclopropylmethyl methyl ester, 46% yield, m.p. 181°–182° C.

Analysis for $C_{21}H_{22}N_2O_4S$; Calculated: C, 63.30; H, 5.57; N, 7.03; Found: C, 63.54; H, 5.61; N, 7.20.

47. (R)-1,4-Dihydro-2,6-dimethyl-4-thieno[3,2-c]pyridin-3-yl-3,5-pyridinedicarboxylic acid, methyl 1-phenylethyl ester, 23% yield, m.p. 199°–202° C.

Analysis for $C_{25}H_{24}N_2O_4S$; Calculated: C, 66.94; H, 5.39; N, 6.25; Found: C, 66.69; H, 5.14; N, 6.13.

48. 1,4-Dihydro-2,6-dimethyl-4-thieno[3,2-c]pyridin-3-yl-3,5-pyridinedicarboxylic acid, methyl 2-propynyl ester, 8% yield, m.p. 211°–214° C.

Analysis for $C_{20}H_{18}N_2O_4S$; Calculated: C, 62.81; H, 4.74; N, 7.33; Found: C, 62.55; H, 4.70; N, 7.08.

49. 1,4-Dihydro-2,6-dimethyl-4-thieno[3,2-c]pyridin-3-yl-3,5-pyridinedicarboxylic acid, methyl 2-methylbutyl ester, 14% yield, m.p. 170°–172° C.

Analysis for $C_{22}H_{26}N_2O_4S$; Calculated: C, 63.75; H, 6.32; N, 6.76; Found: C, 63.99; H, 6.50; N, 6.90.

50. 1,4-Dihydro-2,6-dimethyl-4-thieno[3,2-c]pyridin-3-yl-3,5-pyridinecarboxylic acid, methyl 2-propenyl ester, 16% yield, m.p. 182°–185° C.

Analysis for $C_{20}H_{20}N_2O_4S$; Calculated: C, 62.48; H, 5.24; N, 7.29; Found: C, 62.02; H, 5.25; N, 6.91.

51. 1,4-Dihydro-2,6-dimethyl-4-thieno[3,2-c]pyridin-3-yl-3,5-pyridinedicarboxylic acid, cyclopropylmethyl methyl ester, 10% yield, m.p. 182°–183° C.

Analysis for $C_{21}H_{22}N_2O_4S$; Calculated: C, 63.30; H, 5.57; N, 7.03; Found: C, 63.12; H, 5.42; N, 7.14.

EXAMPLES 52–53

The following compounds were prepared according to the procedure of Example 1B from the appropriate acetoacetate derivative and the corresponding aldehyde.

52. 1,4-Dihydro-2,6-dimethyl-4-thieno[3,2-c]pyridin-3-yl-3,5-pyridinedicarboxylic acid, diethyl ester, 38% yield, m.p. 172.5°–174° C.

Analysis for $C_{20}H_{22}N_2O_4S$; Calculated: C, 62.16; H, 5.74; N, 7.25; Found: C, 62.31; H, 6.01; N, 7.29.

53. 1,4-Dihydro-2,6-dimethyl-4-thieno[3,2-c]pyridin-3-yl-3,5-pyridinedicarboxylic acid, dibutyl ester, 8% yield, m.p. 166°–168° C.

Analysis for $C_{24}H_{30}N_2O_4S$; Calculated: C, 65.13; H, 6.83; N, 6.33; Found: C, 64.92; H, 6.32; N, 6.62.

EXAMPLES 54–55

The following compounds were prepared by the method described in Example 22B from the appropriate dibromomethyl derivative and the corresponding acetoacetate reagent.

54. 1,4-Dihydro-2,6-dimethyl-4-thieno[2,3-c]pyridin-7-yl-3,5-pyridinedicarboxylic acid, diethyl ester, 16% yield, m.p. 205°–210° C. with decomposition. The proton NMR spectrum was consistent with the proposed structure.

Analysis for $C_{20}H_{22}N_2O_4S$; Calculated: C, 62.16; H, 5.74; N, 7.25; Found: C, 58.85; H, 5.65; N, 7.21.

55. 4-(Benzo[b]thien-4-yl)-1,4-dihydro-2,6-dimethyl-3,5-pyridinedicarboxylic acid, diethyl ester, 12% yield, m.p. 177°–179° C.

Analysis for $C_{21}H_{22}NO_4S$; Calculated: C, 65.60; H, 5.77; N, 3.64; Found: C, 65.83; H, 5.99; N, 3.57.

The compounds of formula I are calcium antagonists (calcium-channel blockers) and are particularly useful as antihypertensive agents. They have also been shown to be peripheral and cerebral vasodilators useful in the treatment of stroke, angina, and migraine by preventing vaso-spasm. In addition, the compounds are also useful as antiasthma agents. For example, certain compounds of this invention were examined as to their pharmacodynamic effects in the following test system.

DOG CORONARY ARTERY TEST

Mongrel dogs of either sex and weighing 15 to 30 kg were anesthetized with pentobarbital (35 mg/kg). Each heart was quickly removed through a right thoracotomy and placed in Kreb's bicarbonate solution of the following composition (mM/L): NaCl, 118.2; KCl, 4.6; $CaCl_2.2H_2O$, 1.6; $KH_2PO_4$, 1.2; $MgSO_4.7H_2O$, 1.2; $NaHCO_3$, 24.8; and dextrose, 10.0. The medium was kept at room temperature and saturated with 95% $O_2$/5% $CO_2$. The left anterior descending and circumflex coronary arteries were isolated and used either immediately or stored overnight at 5° C. Arteries were cut into rings approximately 2 to 3 mm wide, placed on 2 L-shaped hooks and mounted in a 10 ml organ bath by attaching one hook to a stationary glass rod and the other hook to a force-displacement transducer. Tissue medium consisted of Kreb's bicarbonate solution maintained at 37° C. and bubbled with 95% $O_2$/5% $CO_2$. Artery rings were equilibrated for 1–2 hours under a resting tension of 3 g. Tissue medium was then changed to one containing 50 mM KCl and 72.8 mM NaCl but otherwise identical to Kreb's bicarbonate solution. After tissues achieved a steady state contractile tension (1–2 hours) a given test agent was added to each bath and concentration-response curves determined. For each added concentration, steady state relaxation was achieved in about 20 minutes; fresh medium was then placed in the bath and the next concentration was added. At the end of the concentration-response curve, tissue medium was changed to one identical to the 50 mM KCl buffer but containing 2.5 mM EGTA and no $CaCl_2.2H_2O$ to obtain complete relaxation of the tissue. Percent relaxation was then determined for each concentration and values producing 50% relaxation ($IC_{50}$) were estimated using a probit analysis. Mean values for $-\log IC_{50}$ were calculated for each agent and are reported in Table 1.

TABLE 1

| Dog Coronary Artery Test | |
|---|---|
| Compound of Example No. | $-\log IC_{50}$ |
| 1 | 3.96 |
| 2 | 4.97 |
| 3 | 7.1 |
| 4 | 5.5 |
| 5 | 7.55 |
| 6 | 6.4 |
| 7 | 6.4 |
| 8 | 6.3 |
| 9 | 7.0 |
| 10 | 6.6 |
| 11 | 6.9 |
| 12 | 7.39 |
| 13 | 6.06 |
| 14 | 5.5 |
| 15 | 5.56 |
| 16 | 6.39 |
| 17 | 7.08 |
| 18 | 5.46 |
| 19 | 7.0 |
| 20 | 7.8 |
| 21 | 7.21 |
| 22 | 4.4 |
| 23 | 5.15 |
| 24 | 7.08 |
| 25 | 5.77 |
| 26 | 6.64 |
| 27 | 6.69 |
| 28 | 6.81 |
| 29 | 5.87 |
| 31 | 6.9 |
| 32 | 4.67 |
| 33 | 7.52 |
| 34 | 6.5 |
| 35 | 6.6 |
| 36 | 5.7 |
| 37 | 6.78 |
| 38 | 6.6 |
| 39 | 6.05 |
| 40 | 7.48 |
| 41 | 7.49 |
| 42 | 7.09 |
| 43 | 7.0 |
| 44 | 7.15 |
| 45 | 6.19 |
| 46 | 7.08 |
| 47 | 7.31 |
| 48 | 7.04 |

TABLE 1-continued

| Dog Coronary Artery Test | |
|---|---|
| Compound of Example No. | −log IC$_{50}$ |
| 50 | 7.39 |
| 51 | 8.12 |
| 52 | 6.94 |
| 53 | 5.97 |
| 54 | 7.1 |
| 55 | 6.82 |

The compounds of this invention may be administered by any number of routes, including the oral, sublingual, subcutaneous, intramuscular, intravenous, transdermal, and rectal routes. The compounds are usually employed in the form of pharmaceutical compositions. Such compositions are prepared in a manner well known in the pharmaceutical art and comprise from about 1 to about 95 percent by weight of at least one active compound of the above Formula I.

Such pharmaceutical compositions comprise as active ingredient a compound of the above formula associated with a pharmaceutically acceptable carrier. In making the compositions, the active ingredient will usually be mixed with a carrier, or diluted by a carrier, or enclosed with a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, by lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of the above formula.

EXAMPLE 56

Hard gelatin capsules are prepared using the following ingredients:

| | per capsule |
|---|---|
| 1,4-dihydro-2,6-dimethyl-4-thieno[2,3-c]pyridin-7-yl-3,5-pyridinedicarboxylic acid, diethyl ester | 250 mg |
| Starch dried | 200 mg |
| Magnesium stearate | 10 mg |
| Total | 460 mg |

The above ingredients are mixed and filled into hard gelatin capsules in 460 mg quantities.

EXAMPLE 57

Capsules each containing 20 mg of medicament are made as follows:

| | per capsule |
|---|---|
| 1,4-dihydro-2,6-dimethyl-4-thieno[3,2-c]pyridin-3-yl-3,5-pyridinedicarboxylic acid, bis-isopropyl ester | 20 mg |
| Starch | 89 mg |
| Microcrystalline cellulose | 89 mg |
| Magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

EXAMPLE 58

Capsules each containing 100 mg of active ingredient are made as follows:

| | per capsule |
|---|---|
| 4-(6-aminobenzo[b]thien-3-yl)-1,4-dihydro-2,6-dimethyl-3,5- | 100 mg |

-continued

| | per capsule |
|---|---|
| pyridinedicarboxylic acid, diethyl ester | |
| Polyoxyethylenesorbitan monooleate | 50 mcg |
| Starch powder | 250 mg |

The above ingredients are thoroughly mixed and are placed in an empty gelatin capsule.

EXAMPLE 59

Tablets each containing 10 mg of active ingredient are made up as follows:

| | per tablet |
|---|---|
| 1,4-dihydro-2,6-dimethyl-4-(6-methylthieno[2,3-c]-pyridin-3-yl)-3,5-pyridine-dicarboxylic acid, methyl propyl ester | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 60

A tablet formula is prepared using the ingredients below:

| | per tablet |
|---|---|
| 4-benzo[b]thien-3-yl-1,4-dihydro-2,6-dimethyl-3,5-pyridinedicarboxylic acid, 3-methyl 5-(2-[methyl(phenylmethyl)amino]ethyl) ester | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 61

Suppositories each containing 25 mg of active ingredient are made as follows:

| | per suppository |
|---|---|
| 1,4-dihydro-2,6-dimethyl-4-thieno[2,3-b]pyridin-3-yl-3,5-pyridinedicarboxylic acid, diethyl ester | 25 mg |

-continued

| | per suppository |
|---|---|
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 62

Suspensions each containing 5 mg of medicament per 5 ml dose are made as follows:

| | per 5 ml of suspension |
|---|---|
| 1,4-dihydro-2,6-dimethyl-4-thieno[3,2-c]pyridin-3-yl-3,5-pyridinedicarboxylic acid, bis(2-methoxyethyl)ester | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 63

An aerosol solution is prepared containing the following components:

| | Weight % |
|---|---|
| 1,4-dihydro-2,6-dimethyl-4-(5-nitrobenzo[b]thien-3-yl)-3,5-pyridinedicarboxylic acid, dimethyl ester | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

I claim:

1. A compound of the formula

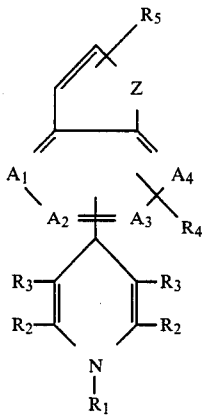

wherein:

R₁ is hydrogen, C₁–C₄ alkyl, or

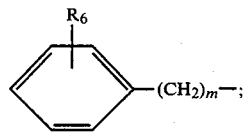

each R₂ is independently hydrogen, methyl, or amino;

each R₃ is independently hydrogen, —COR₇, —CO₂R₇, or —S(O)ₙR₇;

R₄ is hydrogen, methyl, methoxy, halo, nitro, or amino;

R₅ is hydrogen, methyl, methoxy, halo, or C₁–C₄ alkylthio;

R₆ is hydrogen, halo, C₁–C₄ alkoxy, C₁–C₄ alkyl, or nitro;

m is 0, 1, 2, 3, 4;

Z is O, S, or NH;

three or four of A₁, A₂, A₃, and A₄ are CH, and the remaining of A₁, A₂, A₃, and A₄, if any, is N;

R₇ is —alk—(Y—alk—)ₜ—R₈, allyl, propargyl, C₃–C₆ cycloalkyl, phenyl, or phenyl substituted with one to three substituents selected from C₁–C₄ alkyl, C₁–C₄ alkoxy, nitro, or halo;

each "alk" is a straight or branched chain C₁–C₆ alkylene radical;

Y is —O—, —NH—, or a bond;

t is 0 or 1;

R₈ is hydrogen, phenyl, pyridyl, —CN, or —NR₉R₁₀;

R₉ and R₁₀ are independently C₁–C₃ alkyl or benzyl, or when taken together with the nitrogen atom to which they are attached form a pyrrolidino, piperidino, or homopiperidino ring, wherein the dihydropyridine group can be attached to any available carbon atom of the bicyclic ring system, provided that when Z is NH or O, one of A₁, A₂, A₃, and A₄ must be N, and further provided that when Z is S and each of A₁, A₂, A₃, and A₄ is CH, the benzothiophene represented thereby must be attached at the 3- or 4-position thereof to the dihydropyridine group, and pharmaceutically acceptable salts thereof.

2. A compound according to claim 1 wherein A₂ is N and Z is S.

3. The compound of claim 2 which is 1,4-dihydro-2,6-dimethyl-4-thieno[3,2-c]pyridin-3-yl-3,5-pyridinedicarboxylic acid, 3-methyl 5-(1methylethyl)ester, or a pharmaceutically acceptable acid addition salt thereof.

4. The compound of claim 2 which is 1,4-dihydro-2,6-dimethyl-4-thieno[3,2-c]pyridin-3-yl-3,5-pyridinedicarboxylic acid, methyl (S)-1-methylpropyl ester, or a pharmaceutically acceptable acid addition salt thereof.

5. The compound of claim 2 which is 1,4-dihydro-2,6-dimethyl-4-thieno[3,2-c]pyridin-3-yl-3,5-pyridinedicarboxylic acid, cyclopropylmethyl methyl ester, or a pharmaceutically acceptable acid addition salt thereof.

6. The compound of claim 2 which is 1,4-dihydro-2,6-dimethyl-4-thieno[3,2-c]pyridin-3-yl-3,5-pyridinedicarboxylic acid, ethyl methyl ester, or a pharmaceutically acceptable acid addition salt thereof.

7. The compound of claim 2 which is 1,4-dihydro-2,6-dimethyl-4-thieno[3,2-c]pyridin-3-yl-3,5-pyridinedicarboxylic acid, diethyl ester, or a pharmaceutically acceptable acid addition salt thereof.

8. The compound of claim 2 which is 1,4-dihydro-2,6-dimethyl-4-thieno[3,2-c]pyridin-3-yl-3,5-pyridinedicarboxylic acid, methyl 2-propynyl ester, or a pharmaceutically acceptable acid addition salt thereof.

9. A method of causing vasodilation in mammals which comprises administering to a mammal in need of such treatment an effective amount of compound according to claim 1.

10. The method of claim 9 employing the compound 1,4-dihydro-2,6-dimethyl-4-thieno[3,2-c]pyridin-3-yl-3,5-pyridinedicarboxylic acid, 3-methyl 5-(1-methylethyl)ester, or a pharmaceutically acceptable acid addition salt thereof.

11. The method of claim 9 employing the compound 1,4-dihydro-2,6-dimethyl-4-thieno[3,2-c]pyridin-3-yl-3,5-pyridinedicarboxylic acid, methyl (S)-1-methylpropyl ester, or a pharmaceutically acceptable acid addition salt thereof.

12. The method of claim 9 employing the compound 1,4-dihydro-2,6-dimethyl-4-thieno[3,2-c]pyridin-3-yl-3,5-pyridinedicarboxylic acid, cyclopropylmethyl methyl ester, or a pharmaceutically acceptable acid addition salt thereof.

13. The method of claim 9 employing the compound 1,4-dihydro-2,6-dimethyl-4-thieno[3,2-c]pyridin-3-yl-3,5-pyridinedicarboxylic acid, ethyl methyl ester, or a pharmaceutically acceptable acid addition salt thereof.

14. A pharmaceutical formulation useful for causing vasodilation in mammals comprising an effective amount of a compound of claim 1 in association with a pharmaceutically acceptable carrier, diluent, or excipient therefor.

15. A formulation according to claim 14 employing the compound 1,4-dihydro-2,6-dimethyl-4-thieno[3,2-c]pyridin-3-yl-3,5-pyridinedicarboxylic acid, 3-methyl 5-(1-methylethyl)ester, or a pharmaceutically acceptable acid addition salt thereof.

16. A formulation according to claim 14, employing the compound 1,4-dihydro-2,6-dimethyl-4-thieno[3,2-c]pyridin-3-yl-3,5-pyridinedicarboxylic acid, methyl (S)-1-methylpropyl ester, or a pharmaceutically acceptable acid addition salt thereof.

17. A formulation according to claim 14 employing the compound 1,4-dihydro-2,6-dimethyl-4-thieno[3,2-c]pyridin-3-yl-3,5-pyridinedicarboxylic acid, cyclopropylmethyl methyl ester, or a pharmaceutically acceptable acid addition salt thereof.

18. A formulation according to claim 14 employing the compound 1,4-dihydro-2,6-dimethyl-4-thieno[3,2-c]pyridin-3-yl-3,5-pyridinedicarboxylic acid, ethyl methyl ester, or a pharmaceutically acceptable acid addition salt thereof.

19. A formulation according to claim 14 employing the compound 1,4-dihydro-2,6-dimethyl-4-thieno[3,2-c]pyridin-3-yl-3,5-pyridinedicarboxylic acid, diethyl ester, or a pharmaceutically acceptable acid addition salt thereof.

20. A formulation according to claim 14 employing the compound 1,4-dihydro-2,6-dimethyl-4-thieno[3,2-c]pyridin-3-yl-3,5-pyridinedicarboxylic acid, methyl 2-propynyl ester, or a pharmaceutically acceptable acid addition salt thereof.

* * * * *